United States Patent
Cui et al.

(10) Patent No.: US 12,422,798 B1
(45) Date of Patent: Sep. 23, 2025

(54) PROCESS ADJUSTMENT CONTROL METHOD AND SYETEM BASED ON PRODUCTION LINE CO-PRODUCTION

(71) Applicant: HUANENG (TIANJIN) GAS POWER CO., LTD., Tianjin (CN)

(72) Inventors: Pihuan Cui, Tianjin (CN); Xiangping Wang, Tianjin (CN); Zhiqiang Li, Tianjin (CN); Chao Wang, Tianjin (CN); Huiji Song, Tianjin (CN); Xiaomeng Kang, Tianjin (CN); Fanming Deng, Tianjin (CN); Zeyu Tong, Tianjin (CN); Zhe Wang, Tianjin (CN)

(73) Assignee: HUANENG (TIANJIN) GAS POWER CO., LTD., Tianjin (CN)

( * ) Notice: Subject to any disclaimer, the term of this patent is extended or adjusted under 35 U.S.C. 154(b) by 0 days.

(21) Appl. No.: 19/082,151

(22) Filed: Mar. 17, 2025

Related U.S. Application Data (63) Continuation of application No. PCT/CN2025/076618, filed on Feb. 10, 2025.

(30) Foreign Application Priority Data

Oct. 10, 2024 (CN) .......................... 202411407471.4

(51) Int. Cl.
  G05B 13/04 (2006.01)
  C07C 29/00 (2006.01)
  G06F 17/11 (2006.01)

(52) U.S. Cl.
  CPC ............ G05B 13/042 (2013.01); C07C 29/00 (2013.01); G06F 17/11 (2013.01)

(58) Field of Classification Search
  CPC ........ G05B 13/042; C07C 29/00; G06F 17/11
  See application file for complete search history.

(56) References Cited

U.S. PATENT DOCUMENTS

2010/0031558 A1* 2/2010 Goss ........................ C10L 1/026
                                                    44/379
2015/0275727 A1* 10/2015 Hiltzik ............. F02M 35/10222
                                                    95/143

(Continued)

FOREIGN PATENT DOCUMENTS

CN         102557931 A      7/2012
CN         113790101 A     12/2021

(Continued)

*Primary Examiner* — Tameem D Siddiquee (57) ABSTRACT

A process adjustment control method and system based on production line co-production is provided, and relates to the technical field of novel power systems. The method includes: completing full load state operation under load adjustment according to production line co-production, and indirectly adjusting change of power generation load by adjusting ethanol production process load; optimizing load rate provided by gas turbine in a production line co-production process through fuel oil provided by ethanol storage tank; completing a process adjustment control of production line co-production through a mutual feedback mechanism of sensors and a data acquisition model. The disclosure realizes the process adjustment control of the production line co-production, effectively solve the problems of slow response speed and insufficient adjustment precision in the prior art, and improve the automatic adjustment capability of the production line, thus ensuring the efficient operation in a complex and changeable production environment.

4 Claims, 2 Drawing Sheets

(56) References Cited

U.S. PATENT DOCUMENTS

2021/0189965 A1* 6/2021 Lawson .................... F02C 7/26
2022/0088535 A1 3/2022 Mukherjee

FOREIGN PATENT DOCUMENTS

CN         116613809  A      8/2023
WO    WO 2012171176    * 12/2012 ................ C10L 1/04

* cited by examiner

PROCESS ADJUSTMENT CONTROL METHOD AND SYETEM BASED ON PRODUCTION LINE CO-PRODUCTION

CROSS-REFERENCE TO RELATED APPLICATIONS

This application is a continuation of PCT/CN2025/076618, filed on Feb. 10, 2025 and claims priority of Chinese Patent Application No. 202411407471.4, filed on Oct. 10, 2024, the entire contents of which are incorporated herein by reference.

TECHNICAL FIELD

The disclosure relates to the technical field of novel power systems, in particular to a process adjustment control method and system based on production line co-production.

BACKGROUND

With the rapid development of social economy and the continuous upgrading of manufacturing industry, the intelligent production line of new energy has become one of the core driving forces of modern industry. While pursuing efficient production and quality control, enterprises are also facing increasingly complex production process management requirements. The traditional production control method seems to be unable to cope with today's highly dynamic and changeable production environment. Therefore, the demand of society for more intelligent and automatic process adjustment and control methods is increasingly urgent, so as to ensure the improvement of production efficiency and the maximization of resource utilization, and highlight the urgency of new energy technology. Based on this social background, the disclosure proposes a process adjustment and control method and system suitable for a co-generation production line, so as to better meet the demand of modern manufacturing industry for efficient and flexible production.

However, there are some shortcomings in the application of the existing production line co-production process control system. For example, some systems have some problems such as slow response speed and insufficient adjustment accuracy when dealing with complex production processes with multiple variables and parameters. These technical defects limit the overall efficiency and product quality of the production line to a certain extent. Aiming at these problems, the disclosure provides a process adjustment control method and system based on production line co-production, which aims to effectively improve the automatic adjustment capability of the production line and solve the shortcomings in the prior art by optimizing the control algorithm and enhancing the system integration capability.

SUMMARY

In view of the problems existing in the existing process adjustment control method and system based on production line co-production, the disclosure is provided.

Therefore, an object of the disclosure is to provide a process adjustment control method and system based on production line co-production. Aiming at the problems existing in the application process of the existing production line co-production process control system, the disclosure proposes a process adjustment control method based on production line co-production, aiming at effectively improving the automatic adjustment capability of the production line by optimizing the control algorithm and enhancing the system integration capability.

In order to solve the above technical problems, the disclosure provides the following technical scheme:

In the first aspect, the embodiment of the disclosure provides a process adjustment control method based on production line co-production, which includes completing full load state operation under load adjustment according to production line co-production, and indirectly adjusting change of power generation load by adjusting ethanol production process load;

optimizing load rate provided by gas turbine in a production line co-production process through fuel oil provided by ethanol storage tank in a change process of adjusting power generation load, based on rate influence of production line co-production;

adjusting optimized load rate based on the production line co-production in a load adjustment state, and completing a process adjustment control of production line co-production through a mutual feedback mechanism of sensors and a data acquisition model.

As a preferred scheme of the process adjustment control method based on production line co-production according to the disclosure, where: the full load state includes adjusting power generation device load by reducing or increasing ethanol process load under a condition of based on production line co-production ethanol;

where adjusting the power generation device load includes adjusting according to the synthetic gas volume distribution rule of the power generation device, where the synthetic gas volume distribution rule includes building a mathematical model of a system according to operating characteristics of ethanol production line under a full load state, and the mathematical model includes processing load ranges, load change rates, inertia characteristics and production efficiencies of the production line co-production device and the power generation device, and pre-analyzing the mathematical model through a multi-objective optimization algorithm;

the multi-objective optimization algorithm includes optimizing parameters of the synthetic gas volume distribution rule according to multivariate objectives, and calculating based on optimized parameters to obtain the synthetic gas volume distribution rule, and a specific calculation formula of the parameters is:

$$V_{synthetic\ gas\ for\ power\ generation} = \alpha \cdot V_{total\ synthesis\ gas};$$

$$V_{synthesis\ gas\ for\ ethanol} = (1-\alpha) \cdot V_{total\ synthesis\ gas};$$

where $\alpha$ represents parameters, $V_{total\ synthesis\ gas}$ represents total synthesis gas volume, $V_{synthetic\ gas\ for\ power\ generation}$ represents synthesis gas volume of the power generation device, and $V_{synthesis\ gas\ for\ ethanol}$ represents synthesis gas volume of the ethanol production line co-production device.

As a preferred scheme of the process adjustment control method based on production line co-production according to the disclosure, where: adjusting change of power generation load includes decomposing production line co-production when load adjustment being in a full load state, and decomposition includes performing full load production on production line co-production units according to air separation, gasification, purification and desulfurization, and adjusting amplitudes of the power generation device and the ethanol production line co-production device by calculating obtained parameters of synthesis gas volume distribution rule;

where when the system requires to increase load of the power generation device, detecting a current load state of the ethanol production line co-production device by the system, reducing the synthetic gas volume $V_{synthesis\ gas\ for\ ethanol}$ of ethanol production line co-production device and increasing the total synthetic gas volume $V_{total\ synthesis\ gas}$ through an intelligent control system, so as to enhance the power generation load;

when the system requires to reduce the load of the power generation device, detecting a current load state of the ethanol production line co-production device by the system, increasing the synthetic gas volume $V_{synthesis\ gas\ for\ ethanol}$ of ethanol production line co-production device and reducing the total synthetic gas volume $V_{total\ synthesis\ gas}$ through the intelligent control system, so as to reduce the power generation load.

As a preferred scheme of the process adjustment control method based on production line co-production according to the disclosure, where: optimizing load rate provided by the gas turbine in a production line co-production process includes monitoring current load states of the power generation device and the ethanol production line co-production device by using the intelligent control system, and a specific calculation formula for monitoring is:

$$L_{total} = L_{power} + L_{ethanol};$$

where, $L_{total}$ represents load rate after the gas turbine changes in a production line co-production process, $L_{power}$ represents current load of the power generation device, $L_{ethanol}$ represents current load of the ethanol production line co-production device;

when load rate $L_{total}$ after gas turbine changing in a production line co-production process exceeds a preset threshold range of production line co-production, triggering adjustment mechanism of the load rate by the system;

where a preset threshold includes setting safety parameters for current loads of the power generation device and the ethanol production line co-generation device based on safety operation of the system, and analyzing operation states under different load conditions according to a simulation process of the mathematical model, where the simulation process of the mathematical model includes considering load ranges, load change rates, inertia characteristics and production efficiencies of the production line co-generation device and the power generation device in a form of multivariable linear or nonlinear equation set;

a calculation formula of the simulation process of the mathematical model is:

$$\Theta_{threshold} = f(L_{max}, L_{min}, R_{load}, I_{inertia});$$

where, $\Theta_{threshold}$ represents the preset threshold, $L_{max}$ represents a maximum load value of a mathematical model simulation system being born, $L_{min}$ represents a minimum load value of the mathematical model simulation system being withstood, $R_{load}$ represents a rate of load change in the mathematical model simulation system, $I_{inertia}$ represents a response speed of load change in the mathematical model simulation system, and $f(\ )$ represents a multivariate function;

optimizing the preset threshold by adopting the multi-objective optimization algorithm, and calculating to obtain optimized preset threshold, where a specific calculation formula is:

$$\Theta'_{threshpld} = \min\left[\sum_{i=1}^{n} \omega_i \times G_i(\Theta_{threshold})\right];$$

where, $\Theta'_{threshold}$ represents the optimized preset threshold, $G_i(\bullet)$ represents a functional form of multi-objective optimization, $\omega_i$ represents a weight coefficient, n represents a number of terms, and i=1 represents a sum of terms from 1 to n;

then, when $L_{total}\ ?\Theta'_{threshold}$, triggering the adjustment mechanism of the load rate by the system.

As a preferred scheme of the process adjustment control method based on production line co-production according to the disclosure, where: adjusting optimized load rate includes calculating a synthetic gas volume distribution ratio of a power generation device and an ethanol production line co-production device according to a synthetic gas volume distribution rule, and adjusting the load rate of the gas turbine through the fuel oil provided by the ethanol storage tank based on the synthetic gas volume distribution ratio;

where a calculation formula of the synthetic gas volume distribution ratio is:

$$\Delta L_{total} = \frac{P_{max} \times V_{total\ synthesis\ gas}}{V_{total\ synthesis\ gas} + \alpha \times \frac{L_{ethanol}}{L_{power}}} \times \frac{1}{V_{synthetic\ gas\ for\ ethanol}};$$

where $\Delta L_{total}$ represents the synthesis gas volume distribution ratio, and $P_{max}$ represents maximum synthesis gas demand of the power generation device;

when $\Delta L_{total}>0$, the load rate increases, and then, detecting current load state $L_{ethanol}$ of the ethanol production line co-production device;

if $L_{ethanol}>L_{ethanol\_min}$, reducing synthetic gas volume of the ethanol production line co-generation device and increasing synthetic gas volume of the power generation device, so that the ethanol production process load is in a normal state, where $L_{ethanol\_min}$ represents a minimum value of current load of the ethanol production line co-generation device, and then, adjusting load rate of the gas turbine, a specific calculation formula for adjustment is:

$$R_{change} = R_{base} + \beta \times \frac{V_{fuel\_ethanol}}{V_{total\ synthesis\ gas}};$$

where $R_{change}$ represents a load rate of adjusted gas turbine, $R_{base}$ represents a basic load rate, $\beta$ represents a fuel oil adjustment coefficient of a load rate, and $V_{fuel\_ethanol}$ represents fuel oil volume provided by the ethanol storage tank;

when $\Delta L_{total}<0$, the load rate decreases, and then, detecting current load $L_{ethanol}$ of the ethanol production line co-production device;

if $L_{ethanol} < L_{ethanol\_min}$, increasing the synthetic gas volume of the ethanol production line co-production device and reducing the synthetic gas volume of the power generation device, so that the ethanol production process load is in a normal state, $L_{ethanol\_min}$ represents the minimum value of the current load of the ethanol production line co-production device;

and then, adjusting a secondary load rate of the gas turbine, a specific calculation formula for adjustment is:

$$R_{change2} = R_{base} - \gamma \times \frac{V_{fuel\_ethanol}}{V_{total\ synthesis\ gas}};$$

where $R_{change2}$ represents a secondary load rate of the adjusted gas turbine, and $\gamma$ represents a fuel oil adjustment coefficient of the secondary load rate.

As a preferred scheme of the process adjustment control method based on production line co-production according to the disclosure, where: the mutual feedback mechanism includes deploying sensors in the production line co-production process by the system and sending data collected by the sensors to the data acquisition model;

if the system detects data collected by the sensors exceeding set range of one parameter in the production line co-production process, transmitting feedback information to a control system by the data acquisition model, and automatically adjusting the synthetic gas volume distribution ratio by the control system according to the feedback information to obtain a secondary distribution ratio;

secondarily transmitting a secondary distribution ratio result to the data acquisition model through the sensors for analysis, and verifying whether the secondary distribution ratio result reaches expected effect of the synthetic gas volume distribution rule;

if the expected effect fails to standard, triggering the mutual feedback mechanism for N times, if the expected effect reaches standard, secondarily adjusting load rate of the gas turbine by the system according to the secondary distribution ratio result reaching the expected effect.

As a preferred scheme of the process adjustment control method based on production line co-production according to the disclosure, where: secondarily adjusting load rate of the gas turbine includes adjusting load rate of the gas turbine again according to the secondary distribution ratio result:

if $L_{ethanol} > L_{ethanol\_min}$, adjusting load rate of the gas turbine again, and a specific calculation formula for adjustment is:

$$R'_{change} = R_{base} + k_f \times F + \beta \times \frac{V_{fuel\_ethanol}}{V_{total\ synthesis\ gas}};$$

where $R'_{change}$ represents load rate of adjusted gas turbine as the secondary distribution ratio result, $k_f$ represents a fuel oil adjustment coefficient of load rate of secondary adjusted gas turbine, and F represents fuel oil volume provided by the ethanol storage tank of the secondary adjusted gas turbine;

if $L_{ethanol} < L_{ethanol\_min}$, adjusting load rate of the gas turbine again, and a specific calculation formula for adjustment is:

$$R'_{change2} = R_{base} + k_f \times F + \gamma \times \frac{V_{fuel\_ethanol}}{V_{total\ synthesis\ gas}};$$

where $R'_{change2}$ represents a secondary load rate of the adjusted gas turbine as the secondary distribution ratio result.

In a second aspect, an embodiment of the disclosure provides a process adjustment control system based on production line co-production, which includes: an adjustment module, used for completing full load state operation under load adjustment according to production line co-production, and indirectly adjusting change of power generation load by adjusting an ethanol production process load;

an optimization module, used for optimizing load rate provided by gas turbine in a production line co-production process through fuel oil provided by an ethanol storage tank;

a control module, used for adjusting and controlling the production line co-production process through a mutual feedback mechanism of sensors and a data acquisition model.

In a third aspect, an embodiment of the disclosure provides a computer device, which includes a memory and a processor, where a computer program is stored in the memory, where when the processor executes the computer program, any one of steps of the above-mentioned process adjustment control method based on production line co-production is realized.

In the fourth aspect, the embodiment of the disclosure provides a computer-readable storage medium, on which a computer program is stored, where the computer program is executed by a processor, any one of steps of the above-mentioned process adjustment control method based on production line co-production is realized.

The disclosure has the following beneficial effect: by innovatively combining the mutual feedback mechanism of the sensor and the data acquisition model, the disclosure successfully realizes the process adjustment control of the production line co-production, effectively solve the problems of slow response speed and insufficient adjustment precision in the prior art, and obviously improve the automatic adjustment capability of the production line by accurately distributing the synthetic gas volume and optimally adjusting the load rate of the gas turbine, thus ensuring the efficient operation in a complex and changeable production environment. At the same time, based on the introduction of multi-objective optimization algorithm, the disclosure can flexibly respond to the changing requirements of multivariable production processes, and ensure the maximization of resource utilization and the further improvement of production efficiency, thus providing a more intelligent and accurate production control solution for modern manufacturing industry.

BRIEF DESCRIPTION OF THE DRAWINGS

In order to explain the technical scheme of the embodiment of the disclosure more clearly, the drawings needed in the description of the embodiment will be briefly introduced below. Obviously, the drawings in the following description are only some embodiments of the disclosure. For ordinary skilled in the field, other drawings can be obtained according to these drawings without creative work.

Where.

DETAILED DESCRIPTION OF THE EMBODIMENTS

In order to make the above objects, features and advantages of the disclosure more obvious and understandable, the specific embodiments of the disclosure will be described in detail with reference to the attached drawings in the description. Obviously, the described embodiments are a part of the embodiments of the disclosure, but not all of embodiments. Based on the embodiments in the disclosure, all other embodiments obtained by ordinary skilled in the field without creative work should belong to the protection scope of the disclosure In the following description, many specific details are set forth in order to fully understand the disclosure, but the disclosure can also be implemented in other ways different from those described here, and those skilled in the art can make similar promotion without violating the connotation of the disclosure, so the disclosure is not limited by the specific embodiments disclosed below.

Secondly, "one embodiment" or "an embodiment" referred to here refers to a specific feature, structure or characteristic that can be included in at least one implementation of the disclosure. The appearances of "in one embodiment" in different places in this description do not all refer to the same embodiment, nor are they separate or selective embodiments mutually exclusive of other embodiments.

The disclosure will be described in detail with reference to the schematic diagram. When describing the embodiment of the disclosure in detail, for the convenience of explanation, the cross-sectional diagram showing the device structure will not be partially enlarged in general proportion, and the schematic diagram is only an example, which should not limit the scope of protection of the disclosure here. In addition, the three-dimensional dimensions of length, width and depth should be included in the actual production.

At the same time, in the description of the disclosure, it should be noted that the azimuth or positional relationship indicated by the terms "up, down, inside and outside" is based on the azimuth or positional relationship shown in the attached drawings, which is only for the convenience of describing the disclosure and simplifying the description, and does not indicate or imply that the referred device or element must have a specific orientation, be constructed and operated in a specific orientation, so it cannot be understood as a limitation of the disclosure. In addition, the term "first, second or third" is only used for descriptive purposes and cannot be understood as indicating or implying relative importance.

Unless otherwise specified and limited in the disclosure, the term "installation, connecting and connection" should be broadly understood, for example, it can be fixed connection, detachable connection or integral connection, it can also be mechanically, electrically or directly connected, indirectly connected through an intermediate medium, or connected inside two elements. For those ordinary skilled in the art, the specific meanings of the above terms in the disclosure can be understood in specific situations.

Embodiment 1

Figure 1:
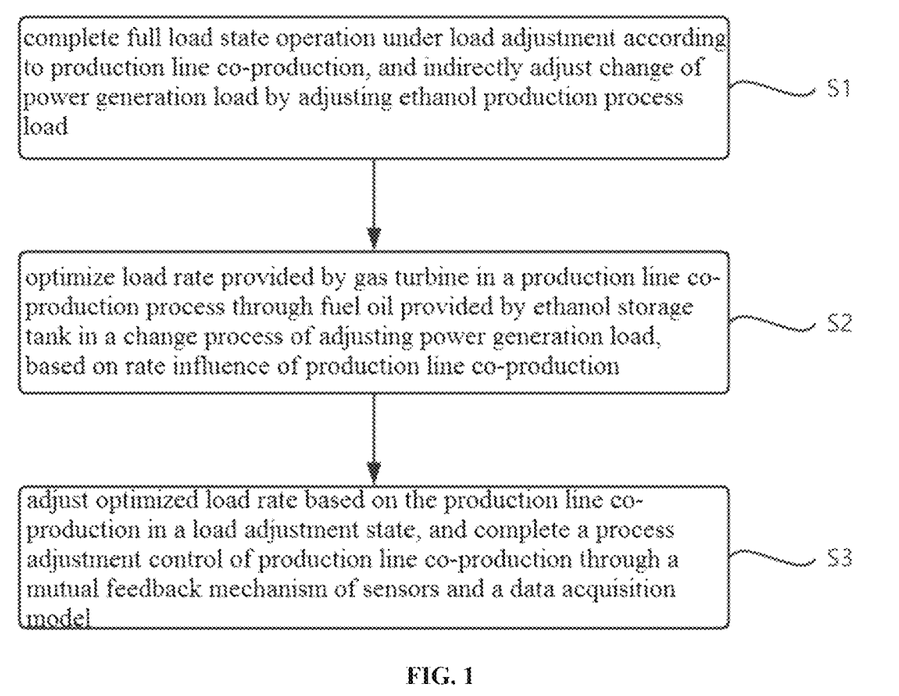
FIG. 1 is a detailed flowchart of a process adjustment control method and system based on production line co-production provided by an embodiment of the disclosure.
Figure 2:
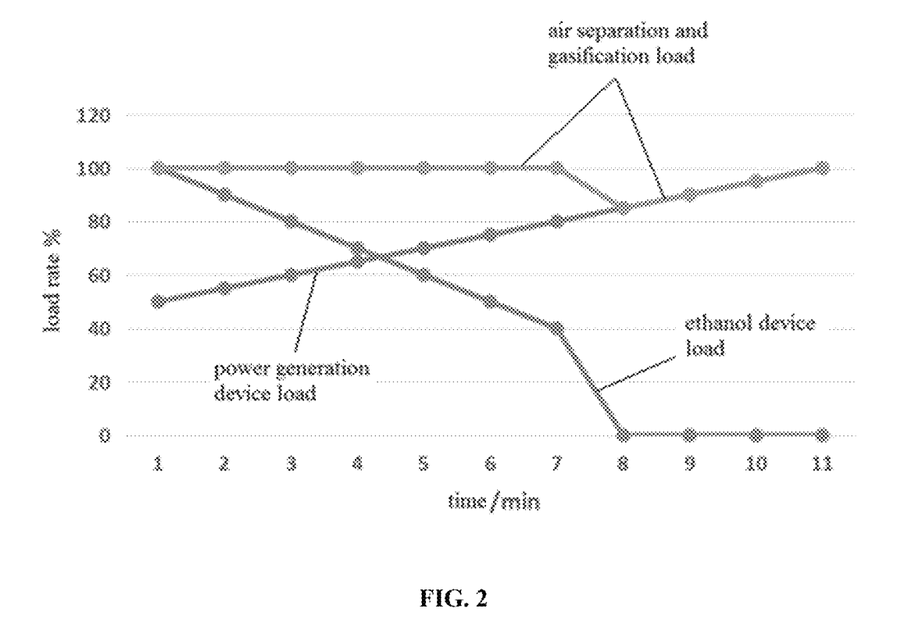
FIG. 2 is a schematic diagram of load data of a process adjustment control method and system based on production line co-production provided by an embodiment of the disclosure.

Referring to FIGS. 1 and 2, this is the first embodiment of the disclosure, which provides a process adjustment control method based on production line co-production, including:

S1: full load state operation is completed under load adjustment according to production line co-production, and change of power generation load is indirectly adjusted by adjusting ethanol production process load.

Where: the full load state includes adjusting power generation device load by reducing or increasing ethanol process load under a condition of based on production line co-production ethanol;

adjusting the power generation device load includes adjusting according to the synthetic gas volume distribution rule of the power generation device, where the synthetic gas volume distribution rule includes building a mathematical model of a system according to operating characteristics of ethanol production line under a full load state, and the mathematical model includes processing load ranges, load change rates, inertia characteristics and production efficiencies of the production line co-production device and the power generation device, and pre-analyzing the mathematical model through a multi-objective optimization algorithm;

the multi-objective optimization algorithm includes optimizing parameters of the synthetic gas volume distribution rule according to multivariate objectives, and calculating based on optimized parameters to obtain the synthetic gas volume distribution rule, and a specific calculation formula of the parameters is:

$$V_{synthetic\ gas\ for\ power\ generation} = \alpha \cdot V_{total\ synthesis\ gas};$$

$$V_{synthesis\ gas\ for\ ethanol} = (1 - \alpha) \cdot V_{total\ synthesis\ gas};$$

where $\alpha$ represents parameters, $V_{total\ synthesis\ gas}$ represents total synthesis gas volume, $V_{synthetic\ gas\ for\ power\ generation}$ represents synthesis gas volume of the power generation device, and $V_{synthesis\ gas\ for\ ethanol}$ represents synthesis gas volume of the ethanol production line co-production device.

Further, in order to realize the full load and efficient operation of the production line co-production system under the load adjustment, the change of power generation load is indirectly adjusted by adjusting the ethanol production process load, Specifically, when the ethanol production line load changes, the system will dynamically adjust the synthetic gas volume of the power generation device based on the current operating state and load characteristics of the ethanol production line to ensure that the whole system can operate stably and efficiently under different load conditions. In order to achieve this goal, the system builds a mathematical model that comprehensively considered the factors such as load range, change rate, inertia characteristics and production efficiency, and optimized the parameters in the model through a multi-objective optimization algorithm. The system can reasonably allocate the synthesis gas volume under the complex conditions of multivariable and multi-objective, and realize the accurate adjustment of the power generation device and the ethanol production line, thus ensuring the optimal operation state of the production line co-production system under different load conditions. This method not only improves the response speed and adjustment accuracy of the system, but also significantly enhances the automatic adjustment ability of the whole production line co-generation system. The load data of the production line co-generation system under load adjustment are shown in the following table 1:

TABLE 1

Load data table of production line co-generation system under load adjustment

| power generation device load % | 50 | 55 | 60 | 65 | 70 | 75 | 80 | 85 | 90 | 95 | 100 |
|---|---|---|---|---|---|---|---|---|---|---|---|
| ethanol device load % | 100 | 90 | 80 | 70 | 60 | 50 | 40 | 0 | 0 | 0 | 0 |
| air separation and gasification load % | 100 | 100 | 100 | 100 | 100 | 100 | 100 | 85 | 90 | 95 | 100 |

According to the load data of each device of the production line co-generation system under different load adjustment conditions, with the power generation device load gradually increasing from 50% to 100%, the ethanol device load shows a gradual downward trend and decreases from 100% to 40%, and then decreases to 0% when the power generation device load reaches 85% or above. At the same time, the air separation and gasification devices load remains at 100% when the power generation device load is 50% to 75%. After the power generation device load reaches 85%, it fluctuates slightly, and finally returns to 100% with the power generation device load reaching 100%. This table reflects the load distribution and adjustment relationship among the devices in the load adjustment process of the production line co-generation system.

S2: load rate provided by gas turbine in a production line co-production process is optimized through fuel oil provided by ethanol storage tank in a change process of adjusting power generation load, based on rate influence of production line co-production.

Where: adjusting change of power generation load includes decomposing production line co-production when load adjustment being in a full load state, and decomposition includes performing full load production on production line co-production units according to air separation, gasification, purification and desulfurization, and adjusting amplitudes of the power generation device and the ethanol production line co-production device by calculating obtained parameters of synthesis gas volume distribution rule;

where when the system requires to increase load of the power generation device, a current load state of the ethanol production line co-production device is detected by the system, the synthetic gas volume $V_{synthesis\ gas\ for\ ethanol}$ of ethanol production line co-production device is reduced and the total synthetic gas volume $V_{total\ synthesis\ gas}$ is increased through an intelligent control system, so as to enhance the power generation load;

when the system requires to reduce the load of the power generation device, a current load state of the ethanol production line co-production device is detected by the system, the synthetic gas volume $V_{synthesis\ gas\ for\ ethanol}$ of ethanol production line co-production device is increased and the total synthetic gas volume $V_{total\ synthesis\ gas}$ is reduced through the intelligent control system, so as to reduce the power generation load.

Further, in the process of adjusting the change of power generation load, the production line co-production system will optimize the load rate of gas turbine through the fuel oil provided by ethanol storage tank according to the rate influence of production line. When the system detects that the power generation device load needs to be increased, the system first analyzes the current load state of ethanol production line. When the power generation device load needs to be increased from 75% to 85%, the system will gradually reduce the synthetic gas volume of ethanol production line from 50% to 0% through the intelligent control system, and at the same time the total synthetic gas volume is increased, so that the power generation device load can be smoothly increased to 85%.

On the contrary, if it is necessary to reduce the power generation device load from 85% to 70%, the system will detect the current load state of the ethanol production line. At this time, the system will gradually increase the synthetic gas volume of the ethanol production line from 0% to 60%, so that the total synthetic gas volume will be reduced, thus reducing the power generation device load to 70%. Through this series of operations, the production line co-generation system can ensure the reasonable load distribution of each device under different load adjustment conditions, and optimize the overall production efficiency.

S2.1: optimizing load rate provided by the gas turbine in a production line co-production process includes monitoring current load states of the power generation device and the ethanol production line co-production device by using the intelligent control system, and a specific calculation formula for monitoring is:

$$L_{total} = L_{power} + L_{ethanol};$$

where, $L_{total}$ represents load rate after the gas turbine changes in a production line co-production process, $L_{power}$ represents current load of the power generation device, $L_{ethanol}$ represents current load of the ethanol production line co-production device;

when load rate $L_{total}$ after gas turbine changing in a production line co-production process exceeds a preset threshold range of production line co-production, adjustment mechanism of the load rate is triggered by the system;

where a preset threshold includes setting safety parameters for current loads of the power generation device and the ethanol production line co-generation device based on safety operation of the system, and analyzing operation states under different load conditions according to a simulation process of the mathematical model, where the simulation process of the mathematical model includes considering load ranges, load change rates, inertia characteristics and production efficiencies of the production line co-generation device and the power generation device in a form of multivariable linear or nonlinear equation set;

a calculation formula of the simulation process of the mathematical model is:

$$\Theta_{threshold} = f(L_{max}, L_{min}, R_{load}, I_{inertia});$$

where, $\Theta_{threshold}$ represents the preset threshold, $L_{max}$ represents a maximum load value of a mathematical model simulation system being born, $L_{min}$ represents a minimum load value of the mathematical model simulation system being withstood, $R_{load}$ represents a rate of load change in the mathematical model simulation system, $I_{inertia}$ represents a response speed of load change in the mathematical model simulation system, and $f(\ )$ represents a multivariate function;

the preset threshold is optimized by adopting the multi-objective optimization algorithm, and calculation is performed to obtain optimized preset threshold, where a specific calculation formula is:

$$\Theta'_{threshold} = \min\left[\sum_{i=1}^{n} \omega_i \times G_i(\Theta_{threshold})\right];$$

where, $\theta'_{threshold}$ represents the optimized preset threshold, $G_i(\cdot)$ represents a functional form of multi-objective optimization, $\omega_i$ represents a weight coefficient, n represents a number of terms, and i=1 represents a sum of terms from 1 to n;

then, when $L_{total} \geq \Theta'_{threshold}$, the adjustment mechanism of the load rate is triggered by the system.

Further, when optimizing the load rate of gas turbine in the process of production line co-production, the system monitors the current load status of power generation device and ethanol production line through intelligent control system. For example, if the current load of power generation device is 70% and the ethanol production line load is 60%, the system will calculate the load rate of gas turbine. If the calculation result shows that the load rate of gas turbine exceeds the preset threshold of the system by 75%, the system will trigger the adjustment mechanism to ensure the safe and efficient operation of the whole production line co-production system.

S3: optimized load rate is adjusted based on the production line co-production in a load adjustment state, and a process adjustment control of production line co-production is completed through a mutual feedback mechanism of sensors and a data acquisition model.

Where: adjusting optimized load rate includes calculating a synthetic gas volume distribution ratio of a power generation device and an ethanol production line co-production device according to a synthetic gas volume distribution rule, and adjusting the load rate of the gas turbine through the fuel oil provided by the ethanol storage tank based on the synthetic gas volume distribution ratio;

a calculation formula of the synthetic gas volume distribution ratio is:

$$\Delta L_{total} = \frac{P_{max} \times V_{total\ synthesis\ gas}}{V_{total\ synthesis\ gas} + \alpha \times \frac{L_{ethanol}}{L_{power}}} \times \frac{1}{V_{synthetic\ gas\ for\ ethanol}};$$

where $\Delta L_{total}$ represents the synthesis gas volume distribution ratio, and $P_{max}$ represents maximum synthesis gas demand of the power generation device;

when $\Delta L_{total} > 0$, the load rate increases, and then, current load state $L_{ethanol}$ of the ethanol production line co-production device is detected;

if $L_{ethanol} > L_{ethanol\_min}$, synthetic gas volume of the ethanol production line co-generation device is reduced and synthetic gas volume of the power generation device is increased, so that the ethanol production process load is in a normal state, where $L_{ethanol\_min}$ represents a minimum value of current load of the ethanol production line co-generation device, and then, load rate of the gas turbine is adjusted, a specific calculation formula for adjustment is;

$$R_{change} = R_{base} + \beta \times \frac{V_{fuel\_ethanol}}{V_{total\ synthesis\ gas}};$$

where $R_{change}$ represents a load rate of adjusted gas turbine, $R_{base}$ represents a basic load rate, $\beta$ represents a fuel oil adjustment coefficient of a load rate, and $V_{fuel\_ethanol}$ represents fuel oil volume provided by the ethanol storage tank;

when $\Delta L_{total} < 0$, the load rate decreases, and then, current load $L_{ethanol}$ of the ethanol production line co-production device is detected;

if $L_{ethanol} < L_{ethanol\_min}$, the synthetic gas volume of the ethanol production line co-production device is increased and the synthetic gas volume of the power generation device is reduced, so that the ethanol production process load is in a normal state, and then, a secondary load rate of the gas turbine is adjusted, a specific calculation formula for adjustment is;

$$R_{change2} = R_{base} - \gamma \times \frac{V_{fuel\_ethanol}}{V_{total\ synthesis\ gas}};$$

where $R_{change2}$ represents a secondary load rate of the adjusted gas turbine, and $\gamma$ represents a fuel oil adjustment coefficient of the secondary load rate.

Furthermore, in the process of load adjustment of production line co-production, the system accurately adjusts the load rate of gas turbine through the feedback mechanism of sensors and the data acquisition model. When the power generation device load needs to be increased from 75% to 85%, the system will reduce the supply of synthetic gas in ethanol production line from 60% to 50%, and at the same time increase the synthetic gas volume of power generation device to support higher power output. At the same time, the adjustment amount of fuel oil is increased by 10% to ensure that the load rate of gas turbine is raised to the required level. If the power generation device load needs to be reduced to 70%, the supply of synthetic gas in ethanol production line will be increased to 60% to maintain its production stability, and the load rate of gas turbine will be reduced accordingly. By reasonably adjusting the amount of synthetic gas and fuel oil, the system can ensure the stability and efficiency of production line co-production under different load conditions.

S3.1: the mutual feedback mechanism includes deploying sensors in the production line co-production process by the system and sending data collected by the sensors to the data acquisition model;

if the system detects data collected by the sensors exceeding set range of one parameter in the production line co-production process, the data acquisition model transmits feedback information to a control system, and the control system automatically adjusts the synthetic gas volume distribution ratio according to the feedback information to obtain a secondary distribution ratio;

the sensors secondarily transmit a secondary distribution ratio result to the data acquisition model for analysis, and whether the secondary distribution ratio result reaches expected effect of the synthetic gas volume distribution rule is verified;

if the expected effect fails to standard, the mutual feedback mechanism is triggered for N times, if the expected effect reaches standard, the system secondarily adjusts load rate of the gas turbine according to the secondary distribution ratio result reaching the expected effect.

Furthermore, in the production line co-production process, the system uses sensors to monitor key parameters in real time. Assuming that the sensor detects that the distribution ratio of synthetic gas volume deviates from the set range, the data acquisition model transmits these data to the control system, and the control system then adjusts the distribution ratio of synthetic gas volume from the initial 70% to 80% according to the feedback information, and the adjusted secondary distribution ratio results are sent back to the data acquisition model through the sensor again for verification. If the secondary distribution ratio fails to achieve the expected effect, the mechanism will be iterated many times (N times) to make adjustments until it meets the expectation. After three adjustments, the system will reach the expected 80% ratio, and the control system will adjust the load rate of the gas turbine accordingly to maintain stable production.

S3.2: secondarily adjusting load rate of the gas turbine includes adjusting load rate of the gas turbine again according to the secondary distribution ratio result, if $L_{ethanol} > L_{ethanol\_min}$, load rate of the gas turbine is adjusted again, and a specific calculation formula for adjustment is:

$$R'_{change} = R_{base} + k_f \times F + \beta \times \frac{V_{fuel\_ethanol}}{V_{total\ synthesis\ gas}};$$

where $R_{change}$ represents load rate of adjusted gas turbine as the secondary distribution ratio result, $k_f$ represents a fuel oil adjustment coefficient of load rate of secondary adjusted gas turbine, and F represents fuel oil volume provided by the ethanol storage tank of the secondary adjusted gas turbine;

if $L_{ethanol} < L_{ethanol\_min}$, load rate of the gas turbine is adjusted again, and a specific calculation formula for adjustment is:

$$R'_{change2} = R_{base} + k_f \times F + \gamma \times \frac{V_{fuel\_ethanol}}{V_{total\ synthesis\ gas}};$$

where $R'_{change2}$ represents a secondary load rate of the adjusted gas turbine as the secondary distribution ratio result.

Preferably, in the process of production line co-production, if the initial adjustment fails to meet the expected effect, the system will adjust the load rate of gas turbine for the second time. When the secondary distribution ratio result initially set by the system is 80%, the control system will adjust the load rate of gas turbine according to this ratio. If the system detects that the load rate needs to be further optimized, the load rate of the gas turbine will be readjusted based on the new data. When it is detected that the actual load rate deviates from the expected 80%, the system will adjust the load rate of the gas turbine and optimize it by increasing or decreasing the fuel oil volume from the ethanol storage tank. Assuming that the original fuel oil adjustment coefficient is 0.5 and the fuel oil volume provided by the ethanol storage tank is 1000 liters, the system will make secondary adjustment according to these data to ensure that the load rate accurately reaches the expected value. Finally, the load rate after the second adjustment will be verified again, and the operation of the gas turbine will be further adjusted to ensure stable and efficient production line co-production.

In a preferred embodiment, a process adjustment control system based on production line co-production is provided, the system includes: an adjustment module, used for completing full load state operation under load adjustment according to production line co-production, and indirectly adjusting change of power generation load by adjusting an ethanol production process load; an optimization module, used for optimizing load rate provided by gas turbine in a production line co-production process through fuel oil provided by an ethanol storage tank; a control module, used for adjusting and controlling the production line co-production process through a mutual feedback mechanism of sensors and a data acquisition model.

The above-mentioned unit modules can be embedded in or independent of the processor in the computer device in the form of hardware, or stored in the memory in the computer device in the form of software, so as to facilitate the processor to call and execute the operations corresponding to the above-mentioned modules.

The computer device can be a terminal, and includes a processor, a memory, a communication interface, a display screen and an input device connected through a system bus. where the processor of the computer device is used for providing computing and control capabilities. The memory of the computer device includes a nonvolatile storage medium and an internal memory. The nonvolatile storage medium stores an operating system and a computer program. The internal memory provides an environment for the operation of the operating system and computer programs in the nonvolatile storage medium. The communication interface of the computer device is used for wired or wireless communication with external terminals, and the wireless mode can be realized by WIFI, operator network, NFC (Near Field Communication) or other technologies. The display screen of the computer device can be a liquid crystal display screen or an electronic ink display screen, and the input device of the computer device can be a touch layer covered on the display screen, a button, a trackball or a touchpad arranged on the shell of the computer device, and also be an external keyboard, touchpad or mouse.

To sum up, by innovatively combining the mutual feedback mechanism of the sensors and the data acquisition model, the disclosure successfully realizes the process adjustment control of the production line co-production, and effectively solves the problems of slow response speed and insufficient adjustment precision in the prior art. Through the accurate distribution of the synthetic gas volume and the optimal adjustment of the gas turbine load rate, the disclosure significantly improves the automatic adjustment capability of the production line and ensures the efficient operation in a complex and changeable production environment. At the same time, based on the introduction of multi-objective optimization algorithm, the disclosure can flexibly respond to the changing requirements of multivariable production processes, and ensure the maximization of resource utilization and the further improvement of production efficiency, thus providing a more intelligent and accurate production control solution for modern manufacturing industry.

Embodiment 2

Referring to FIGS. 1 and 2, this is the second embodiment of the disclosure, which provides a process adjustment control method based on production line co-production. In order to verify the beneficial effects of the disclosure, scientific demonstration is conducted through simulation experiments.

In the experimental process of verifying the disclosure, a plurality of sensors are deployed in the production line co-production system to monitor the load status of the power generation device and the ethanol production line co-production device in real time. At the beginning of the experiment, the system sets the load target of the power generation device as 75% and the load of the ethanol production line co-production device as 60%, and the synthetic gas volume distribution ratio is calculated according to the synthetic gas volume distribution rule, and is set as 85%.

In the initial adjustment stage, the system automatically adjusts the load rate of the gas turbine according to the set proportion, and sets the fuel oil volume provided by the ethanol storage tank to 1200 liters. The experimental data show that the load rate of the power generation device is increased to 70% under this setting, but the system detects that the proportion of synthetic gas volume is deviated from the expectation, and the actual load rate reaches 67%, which is lower than the target load rate.

The system triggers the secondary adjustment mechanism. In the secondary adjustment stage, the control system adjusts the feedback secondary distribution ratio to 82%, and optimizes the gas turbine load rate again. The fuel oil adjustment coefficient is adjusted to 0.6, and the fuel oil volume provided by the ethanol storage tank is increased to 1300 liters. After the secondary adjustment, the load rate of the power generation device is increased to 74%, which is close to the expected target. After the secondary adjustment, the gap between the actual load rate and the target load rate is reduced to 3%, which meets the expected effect of the system, the system ensures that the load rate reaches the set value through N times of mutual feedback mechanism, and maintains a stable production line co-production effect during the whole experiment, thus verifying the effectiveness and optimization ability of the technical scheme. The recorded data of experimental data adjustment are shown in the following table 2:

TABLE 2

| | | | | data table of experimental data adjustment record | | | | |
|---|---|---|---|---|---|---|---|---|
| experimental stage | power generation device load target | ethanol production linel oad | preliminary synthesis gas volume distribution ratio | preliminary fuel oil volume (liter) | preliminary load rate | secondary distribution ratio | secondary fuel oil volume (liter) | secondary load rate |
| preliminary adjustment stage | 75% | 60% | 85% | 1200 | 70% | 82% | 1300 | 74% |
| secondary adjustment stage | 80% | 55% | 80% | 1250 | 72% | 78% | 1350 | 76% |
| actual load rate | 78% | 58% | 82% | 1270 | 71% | 80% | 1320 | 75% |
| load rate target gap | 0 | 0 | 0 | 0 | 2% | 0 | 0 | 1% |

During the experiment, the load adjustment of power generation device and ethanol production line is tested, and the table shows the load changes of ethanol device, air separation and gasification device under different power generation device load percentages of 50% to 100%. When the power generation device load is gradually increased, the ethanol device load is gradually reduced from 100% to 0%, while the load of the air separation and gasification devices is maintained at 100% when the power generation device load is low, and gradually decreased to 85% with the increase of the power generation device load. The data reflects the dynamic change of each device load during the load adjustment process, and verifies the effectiveness of the optimized load adjustment mechanism. Compared with the prior art, the disclosure is shown in the following table 3:

TABLE 3 comparison table between the disclosure and the prior art

| characteristic | the technical scheme of the disclosure | prior art |
|---|---|---|
| load adjustment accuracy | high-precision real-time load adjustment, it is optimized by intelligent control system | the load adjustment accuracy is low, and it often depends on manual intervention and empirical judgment |
| data feedback mechanism | dynamic feedback mechanism is implemented, and real-time adjustment is performed through sensors and the data acquisition model | the feedback mechanism is not real-time, and the data processing and adjustment process is slow |
| synthesis gas volume distribution | multi-objective optimization algorithm is used to optimize the synthetic gas volume distribution ratio to meet different load requirements | the synthetic gas volume distribution rule is fixed, so it is difficult to adapt to load changes |
| adjustment mode | gas turbine load rate is dynamically adjusted through fuel oil provided by ethanol storage tank | the adjustment mode is single and it depends on the fixed load rate adjustment strategy |
| load adjustment range | it is flexibly adjusted under full load state, a wide load range is covered | the adjustment range is limited, it cannot operate effectively under extreme load state |
| experimental verification | based on experimental data, the optimization effect is verified, and data drives decision-making | experimental verification is insufficient, and the effect depends on theoretical analysis and empirical data |

The disclosure is superior to the prior art in the aspect of load adjustment, and has the advantages of real-time accurate adjustment, high flexibility and dynamic optimization. Through the intelligent control system and the data feedback mechanism, the disclosure can quickly adapt to the load change, and the load rate of the gas turbine is adjusted through the fuel oil of the ethanol storage tank, so as to ensure effective adjustment in the full load state and improve the efficiency and accuracy of load adjustment.

It should be noted that the above embodiments are only used to illustrate the technical scheme of the disclosure, but not to limit it. Although the disclosure has been described in detail with reference to the preferred embodiments, those skilled in the art should understand that the technical scheme of the disclosure can be modified or replaced by equivalents without departing from the spirit and scope of the technical scheme of the disclosure, which should be included in the scope of the claims of the disclosure.

The invention claimed is:

1. A process adjustment control method based on production line co-production, comprising:

completing full load state operation under load adjustment according to production line co-production, and indirectly adjusting change of power generation load by adjusting ethanol production process load;

optimizing load rate provided by gas turbine in a production line co-production process through fuel oil provided by ethanol storage tank in a change process of adjusting power generation load, based on rate influence of production line co-production;

adjusting optimized load rate based on the production line co-production in a load adjustment state, and completing a process adjustment control of production line co-production through a mutual feedback mechanism of sensors and a data acquisition model;

wherein adjusting optimized load rate comprises calculating a synthetic gas volume distribution ratio of a power generation device and an ethanol production line co-production device according to a synthetic gas volume distribution rule, and adjusting the load rate of the gas turbine through the fuel oil provided by the ethanol storage tank based on the synthetic gas volume distribution ratio;

wherein a calculation formula of the synthetic gas volume distribution ratio is:

$$\Delta L_{total} = \frac{P_{max} \times V_{total\ synthesis\ gas}}{V_{total\ synthesis\ gas} + \alpha \times \frac{L_{ethanol}}{L_{power}}} \times \frac{1}{V_{synthetic\ gas\ for\ ethanol}};$$

wherein $\Delta L_{total}$ represents the synthesis gas volume distribution ratio, and $P_{max}$ represents maximum synthesis gas demand of the power generation device;

when $\Delta L_{total} > 0$, the load rate increases, and then, detecting current load state $L_{ethanol}$ of the ethanol production line co-production device;

if $L_{ethanol} > L_{ethanol\_min}$, reducing synthetic gas volume of the ethanol production line co-generation device and increasing synthetic gas volume of the power generation device, so that the ethanol production process load is in a normal state, wherein $L_{ethanol\_min}$ represents a minimum value of current load of the ethanol production line co-generation device, and then, adjusting load rate of the gas turbine, a specific calculation formula for adjustment is:

$$R_{change} = R_{base} + \beta \times \frac{V_{fuel\_ethanol}}{V_{total\ synthesis\ gas}};$$

wherein $R_{change}$ represents a load rate of adjusted gas turbine, $R_{base}$ represents a basic load rate, β represents a fuel oil adjustment coefficient of a load rate, and $V_{fuel\_ethanol}$ represents fuel oil volume provided by the ethanol storage tank;

when $\Delta L_{total} < 0$, the load rate decreases, and then, detecting current load $L_{ethanol}$ of the ethanol production line co-production device;

if $L_{ethanol} < L_{ethanol\_min}$, increasing the synthetic gas volume of the ethanol production line co-production device and reducing the synthetic gas volume of the power generation device, so that the ethanol production process load is in a normal state, and then, adjusting a secondary load rate of the gas turbine, a specific calculation formula for adjustment is:

$$R_{change2} = R_{base} - \gamma \times \frac{V_{fuel\_ethanol}}{V_{total\ synthesis\ gas}};$$

wherein $R_{change2}$ represents a secondary load rate of the adjusted gas turbine, and γ represents a fuel oil adjustment coefficient of the secondary load rate;

the full load state comprises adjusting power generation device load by reducing or increasing ethanol process load under a condition of based on production line co-production ethanol;

wherein adjusting the power generation device load comprises adjusting according to the synthetic gas volume distribution rule of the power generation device, wherein the synthetic gas volume distribution rule comprises building a mathematical model of a system according to operating characteristics of ethanol production line under a full load state, and the mathematical model comprises processing load ranges, load change rates, inertia characteristics and production efficiencies of the production line co-production device and the power generation device, and pre-analyzing the mathematical model through a multi-objective optimization algorithm;

the multi-objective optimization algorithm comprises optimizing parameters of the synthetic gas volume distribution rule according to multivariate objectives, and calculating based on optimized parameters to obtain the synthetic gas volume distribution rule, and a specific calculation formula of the parameters is:

$$V_{synthetic\ gas\ for\ power\ generation} = \alpha \cdot V_{total\ synthetic\ gas};$$

wherein α represents parameters, $V_{total\ synthetic\ gas}$ represents total synthesis gas volume, $V_{synthetic\ gas\ for\ power\ generation}$ represents synthesis gas volume of the power generation device, and $V_{synthetic\ gas\ for\ ethanol}$ represents synthesis gas volume of the ethanol production line co-production device;

adjusting change of power generation load comprises decomposing production line co-production when load adjustment being in a full load state, and decomposition comprises performing full load production on production line co-production units according to air separation, gasification, purification and desulfurization, and adjusting amplitudes of the power generation device and the ethanol production line co-production device by calculating obtained parameters of synthesis gas volume distribution rule;

wherein when the system requires to increase load of the power generation device, detecting a current load state of the ethanol production line co-production device by the system, reducing the synthetic gas volume $V_{synthetic\ gas\ for\ ethanol}$ of ethanol production line co-production device and increasing the total synthetic gas volume $V_{total\ synthetic\ gas}$ through an intelligent control system, so as to enhance the power generation load;

when the system requires to reduce the load of the power generation device, detecting a current load state of the ethanol production line co-production device by the system, increasing the synthetic gas volume $V_{synthetic\ gas\ for\ ethanol}$ of ethanol production line co-production device and reducing the total synthetic gas volume $V_{total\ synthetic\ gas}$ through the intelligent control system, so as to reduce the power generation load.

2. The process adjustment control method based on production line co-production according to claim 1, wherein optimizing load rate provided by the gas turbine in a production line co-production process comprises monitoring current load states of the power generation device and the ethanol production line co-production device by using the intelligent control system, and a specific calculation formula for monitoring is:

$$L_{total} = L_{power} + L_{ethanol};$$

wherein, $L_{total}$ represents load rate after the gas turbine changes in a production line co-production process, $L_{power}$ represents current load of the power generation device, $L_{ethanol}$ represents current load of the ethanol production line co-production device;

when load rate $L_{total}$ after gas turbine changing in a production line co-production process exceeds a preset threshold range of production line co-production, triggering adjustment mechanism of the load rate by the system;

wherein a preset threshold comprises setting safety parameters for current loads of the power generation device and the ethanol production line co-generation device based on safety operation of the system, and analyzing operation states under different load conditions according to a simulation process of the mathematical model, wherein the simulation process of the mathematical model comprises considering load ranges, load change rates, inertia characteristics and production efficiencies of the production line co-generation device and the power generation device in a form of multivariable linear or nonlinear equation set;

a calculation formula of the simulation process of the mathematical model is:

$$\Theta_{threshold} = f(L_{max}, L_{min}, R_{load}, I_{inertia});$$

wherein, $\Theta_{threshold}$ represents the preset threshold, $L_{max}$ represents a maximum load value of a mathematical model simulation system being born, $L_{min}$ represents a minimum load value of the mathematical model simulation system being withstood, $R_{load}$ represents a rate of load change in the mathematical model simulation system, $I_{inertia}$ represents a response speed of load change in the mathematical model simulation system, and $f(\ )$ represents a multivariate function;

optimizing the preset threshold by adopting the multi-objective optimization algorithm, and calculating to obtain optimized preset threshold, wherein a specific calculation formula is:

$$\Theta'_{threshpld} = \min\left[\sum_{i=1}^{n} \omega_i \times G_i(\Theta_{threshold})\right];$$

wherein, $\theta'_{threshold}$ represents the optimized preset threshold, $G_i(\bullet)$ represents a functional form of multi-objective optimization, $\omega_i$ represents a weight coefficient, n represents a number of terms, and i=1 represents a sum of terms from 1 to n;

then, when $L_{total} \geq \Theta'_{threshold}$, triggering the adjustment mechanism of the load rate by the system.

3. The process adjustment control method based on production line co-production according to claim 2, wherein the mutual feedback mechanism comprises deploying sensors in the production line co-production process by the system and sending data collected by the sensors to the data acquisition model;

if the system detects data collected by the sensors exceeding set range of one parameter in the production line co-production process, transmitting feedback information to a control system by the data acquisition model, and automatically adjusting the synthetic gas volume distribution ratio by the control system according to the feedback information to obtain a secondary distribution ratio;

secondarily transmitting a secondary distribution ratio result to the data acquisition model through the sensors for analysis, and verifying whether the secondary distribution ratio result reaches expected effect of the synthetic gas volume distribution rule;

if the expected effect fails to standard, triggering the mutual feedback mechanism for N times, if the expected effect reaches standard, secondarily adjusting load rate of the gas turbine by the system according to the secondary distribution ratio result reaching the expected effect.

4. The process adjustment control method based on production line co-production according to claim 3, wherein secondarily adjusting load rate of the gas turbine comprises adjusting load rate of the gas turbine again according to the secondary distribution ratio result;

if $L_{ethanol} > L_{ethanol\_min}$, adjusting load rate of the gas turbine again, and a specific calculation formula for adjustment is:

$$R'_{change} = R_{base} + k_f \times F + \beta \times \frac{V_{fuel\_ethanol}}{V_{total\ synthesis\ gas}};$$

wherein $R'_{change}$ represents load rate of adjusted gas turbine as the secondary distribution ratio result, $k_f$ represents a fuel oil adjustment coefficient of load rate of secondary adjusted gas turbine, and F represents fuel oil volume provided by the ethanol storage tank of the secondary adjusted gas turbine;

if $L_{ethanol} < L_{ethanol\_min}$, adjusting load rate of the gas turbine again, and a specific calculation formula for adjustment is:

$$R'_{change2} = R_{base} + k_f \times F + \gamma \times \frac{V_{fuel\_ethanol}}{V_{total\ synthesis\ gas}};$$

wherein $R'_{change2}$ represents a secondary load rate of the adjusted gas turbine as the secondary distribution ratio result.

\* \* \* \* \*